United States Patent
Wu et al.

(10) Patent No.: US 12,329,720 B2
(45) Date of Patent: Jun. 17, 2025

(54) DOSING SYSTEMS AND APPROACHES

(71) Applicant: AMGEN INC., Thousand Oaks, CA (US)

(72) Inventors: Chia-Jung Wu, Redondo Beach, CA (US); Nicholas J. Clark, Thousand Oaks, CA (US); Ronak Maheshwari, Thousand Oaks, CA (US); Heather N. Franey, Ventura, CA (US)

(73) Assignee: AMGEN INC., Thousand Oaks, CA (US)

( * ) Notice: Subject to any disclaimer, the term of this patent is extended or adjusted under 35 U.S.C. 154(b) by 1278 days.

(21) Appl. No.: 16/782,306

(22) Filed: Feb. 5, 2020

(65) Prior Publication Data
US 2020/0253823 A1 Aug. 13, 2020

Related U.S. Application Data

(60) Provisional application No. 62/804,447, filed on Feb. 12, 2019.

(51) Int. Cl.
*A61J 1/10* (2006.01)
*A61J 1/14* (2023.01)
(Continued)

(52) U.S. Cl.
CPC ............... *A61J 1/10* (2013.01); *A61J 1/1487* (2015.05); *A61J 1/16* (2013.01); *A61M 5/148* (2013.01)

(58) Field of Classification Search
CPC .... A61J 1/10; A61J 1/16; A61J 1/1487; A61J 1/1475; A61J 1/1493; A61M 5/1413;
(Continued)

(56) References Cited

U.S. PATENT DOCUMENTS 4,044,983 A * 8/1977 Francis ............... A61M 5/1415
248/318
6,068,617 A * 5/2000 Richmond ............ A61J 1/2089
604/153
(Continued)

FOREIGN PATENT DOCUMENTS

AU 2003204462 B2 9/2005
JP 2016036415 A 3/2016
(Continued)

OTHER PUBLICATIONS

Rapid Response Report: Summary With Critical Appraisal: Closed-System Transfer Devices for the Handling of Hazardous Drugs: A Review of the Clinical and Cost-Effectiveness and Guidelines, Published May 7, 2015. (Year: 2015).*
(Continued)

*Primary Examiner* — Ariana Zimbouski
(74) *Attorney, Agent, or Firm* — MARSHALL, GERSTEIN & BORUN LLP

(57) ABSTRACT

A drug delivery system includes a delivery container, a first drug insertion port, at least one additional drug insertion port, and an IV connection port. The delivery container includes upper, lower, first side, and second side portions, and further includes a tapered region extending between the first side portion and the second side portion. The first drug insertion port is positioned at the lower portion of the delivery container and has a first coupling mechanism. The at least one additional drug insertion port is also positioned at the lower portion of the delivery container, but includes a second coupling mechanism that is different than the first coupling mechanism. The IV connection port is positioned at the lower portion of the delivery container adjacent to a lower portion of the tapered region.

19 Claims, 3 Drawing Sheets

(51) Int. Cl.
*A61J 1/16* (2023.01)
*A61M 5/148* (2006.01)

(58) Field of Classification Search
CPC ...... A61M 5/14; A61M 5/1417; A61M 5/148; A61M 5/1415; A61M 5/14244; A61M 2005/14268; A61M 2005/1416; A61M 39/10; A61M 2205/123
See application file for complete search history.

(56) References Cited

U.S. PATENT DOCUMENTS

| | | | | |
|---|---|---|---|---|
| 6,179,823 | B1* | 1/2001 | Niedospial, Jr. | A61J 1/10 604/408 |
| 2005/0283123 | A1* | 12/2005 | Lyde | A61M 5/40 604/254 |
| 2006/0100578 | A1 | 5/2006 | Lieberman | |
| 2013/0289496 | A1* | 10/2013 | Langan | G09F 3/10 604/257 |
| 2014/0031976 | A1* | 1/2014 | Reinhardt | G16H 40/60 700/239 |
| 2016/0068591 | A1* | 3/2016 | Anderson | A61K 39/40 424/139.1 |
| 2016/0206511 | A1* | 7/2016 | Garfield | A61J 1/2089 |
| 2017/0202740 | A1* | 7/2017 | Yoshida | B32B 3/08 |
| 2018/0021218 | A1 | 1/2018 | Brosch et al. | |

FOREIGN PATENT DOCUMENTS

| | | |
|---|---|---|
| JP | 2017502795 A | 1/2017 |
| KR | 101346532 * | 12/2013 |
| WO | WO-2015077184 A1 | 5/2015 |
| WO | WO-2017/005265 A1 | 1/2017 |

OTHER PUBLICATIONS

International Application No. PCT/US2020/016714, International Search Report and Written Opinion, dated Apr. 20, 2020.
Japanese Patent Application No. 2021-545389, Office Action, dated Jan. 9, 2024.

* cited by examiner

DOSING SYSTEMS AND APPROACHES

CROSS-REFERENCE TO RELATED APPLICATION

Priority is claimed to U.S. Provisional Patent Application No. 62/804,447 filed Feb. 12, 2019, the entire contents of which are hereby incorporated herein by reference.

FIELD OF DISCLOSURE

The present disclosure generally relates to drug delivery systems and methods. More particularly, the present disclosure relates to improved approaches for preparing and delivering dosing systems.

BACKGROUND

Drugs are administered to treat a variety of conditions and diseases. Intravenous ("IV") therapy is a drug dosing process that delivers drugs directly into a patient's vein using an infusion contained in a container (e.g., a pliable bag). These processes may be performed in a healthcare facility, or in some instances, at remote locations such as a patient's home. Oftentimes, a healthcare professional must prepare the drug by mixing numerous ingredients prior to administration of the drug. Existing systems typically involve a lengthy drug preparation process involving multiple steps. Further, in some environments where extended drug dosings are required involving sequential administration of drugs in multiple containers, it may be necessary to swap these containers while ensuring the entire contents of each container is administered to the patient.

As described in more detail below, the present disclosure sets forth systems and methods for patient monitoring and interventional dosing techniques embodying advantageous alternatives to existing systems and methods, and that may address one or more of the challenges or needs mentioned herein, as well as provide other benefits and advantages.

SUMMARY

In accordance with a first aspect, a drug delivery system includes a delivery container, a first drug insertion port, at least one additional drug insertion port, and an IV connection port. The delivery container includes upper, lower, first side, and second side portions, and further includes a tapered region extending between the first side portion and the second side portion. The first drug insertion port is positioned at the lower portion of the delivery container and has a first coupling mechanism. At least one additional drug insertion port is also positioned at the lower portion of the delivery container, but includes a second coupling mechanism that is different than the first coupling mechanism. The IV connection port is positioned at the lower portion of the delivery container adjacent to a lower portion of the tapered region.

In some examples, the first coupling mechanism is in the form of a luer lock mechanism. The second coupling mechanism may be a closed system transfer device ("CSTD"). In some examples, the CSTD is in the form of a standard 13 mm port that couples to at least one of a 2 R iso-vial or a 13 mm CTSD. In other examples, the CSTD is in the form of a standard 20 mm port that couples to at least one of an iso-vial or a 20 mm CSTD. Other examples are possible.

In some of these examples, the system further includes a rigid container that defines an inner volume. The rigid container has an upper portion and a lower portion that includes an opening to accommodate at least one of the IV connection port or an IV line. In some forms, the delivery container further includes at least one opening formed in the upper portion and the rigid container additionally includes at least one mounting post that is dimensioned to receive at least one opening to operably secure the delivery container within the inner volume of the rigid container. In some examples, the rigid container may include at least one securing strap member. In some approaches, the rigid container also includes an opening at the upper portion to accommodate a portion of the delivery container.

In some examples, the delivery container may be empty. In other approaches, the delivery container contains a saline solution and an intravenous stabilizing solution. In yet other examples, the delivery container contains the saline solution, an intravenous stabilizing solution, and a preservative.

In accordance with another aspect, a drug delivery system includes a delivery container, a first drug insertion port, at least one additional drug insertion port, an IV connection port, and a rigid container. The delivery container includes upper, lower, first side, and second side portions, and additionally includes a tapered region extending between the first side portion and the second side portion and at least one opening formed in the upper portion thereof. The first drug insertion port is positioned at the lower portion of the delivery container and has a first coupling mechanism. At least one additional drug insertion port is also positioned at the lower portion of the delivery container, but includes a second coupling mechanism that is different than the first coupling mechanism. The IV connection port is positioned at the lower portion of the delivery container adjacent to a lower portion of the tapered region. The rigid container defines an inner volume and has upper and lower portions. The upper portion includes at least one mounting post that is dimensioned to receive the at least one opening of the delivery container to operably secure the delivery container within the inner volume of the rigid container. The lower portion of the rigid container includes an opening to accommodate at least one of the IV connection port or an IV line.

BRIEF DESCRIPTION OF THE DRAWINGS

The above needs are at least partially met through provision of the drug delivery system described in the following detailed description, particularly when studied in conjunction with the drawings, wherein.

Figure 1:
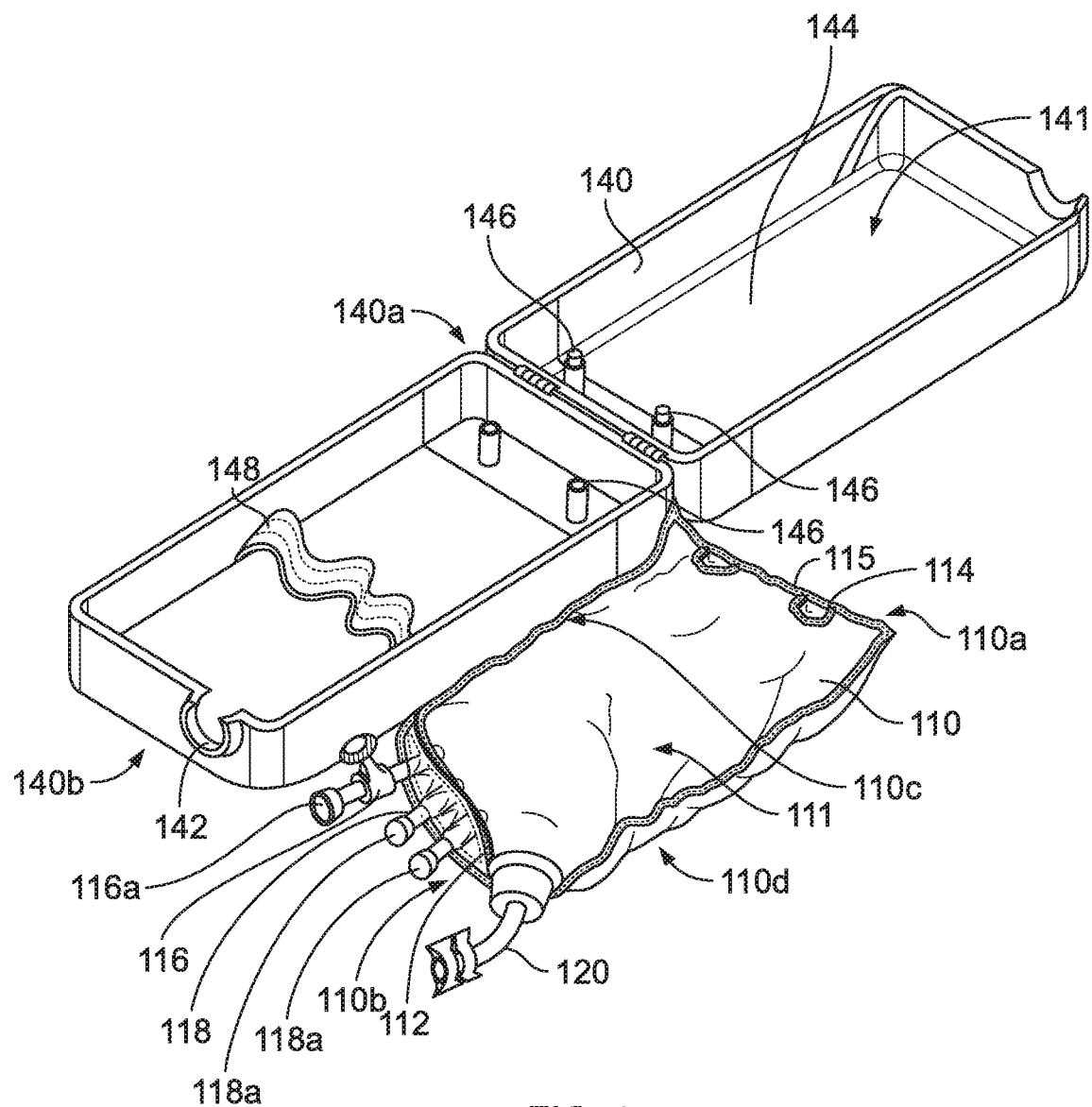
FIG. 1 illustrates an example drug delivery system in accordance with various embodiments.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Turning to the figures, pursuant to these various embodiments, a drug delivery system 100 can include a delivery container 110 and a rigid container 140, which could also be considered a case, a housing, a cover, etc. The system 100 may be used in intravenous, subcutaneous, intra-arterial, intramuscular, and/or epidural delivery approaches having delivery times between approximately five minutes and approximately eight hours. The delivery container 110 includes an upper portion 110a, a lower portion 110b, a first side portion 110c, and a second side portion 110d. The delivery container 110 further includes a tapered region 112 extending a distance between the first side portion 110c and the second side portion 110d. The delivery container is in the form of a flexible and/or pliable bag that includes an interior cavity 111 to accommodate a drug 101 contained therein to be delivered to a patient. In some versions, the interior cavity 111 is sterile. In some versions, the delivery container is constructed similar to a conventional IV bag, and can be formed from one or possibly two pieces of bag film bonded together at seams extending along its perimeter thereby defining the interior cavity 111 for material storage.

In the illustrated example, the tapered region 112 includes a higher portion 112a adjacent the first side portion 110c of the delivery container 110, and a lower portion 112b adjacent both the second side portion 110d and the lower portion 110b of the delivery container 110. From the lower portion 112b, the tapered region 112 extends upwardly to the upper portion 112a adjacent the first side portion 110c. The tapered region 112 may form an angle "α" relative to the lower portion 110b of the delivery container 110. In some examples, the angle α may be between approximately 100° and approximately 150°. Other examples are possible. Further, the tapered region may extend any length of the first side portion 110c such as, for example, approximately 25%. As a result, the delivery container 110 is generally trapezoidal in shape. While the illustrated example delivery container 110 includes a tapered region 112 that terminates at a portion of the lower portion 110b to create a generally flat surface, in other examples, the tapered region 112 may extend the entire length between the first and second sides 110c, 110d. And while the tapered region 112 depicted in this version extends entirely between the first and second side portions 110c, 110d, the tapered region 112 in other versions may only extend partially between the first and second side portions 110c, 110d. Furthermore, while the tapered region 112 is linear in shape, in other versions, other shapes are possible, including V-shaped or U-shaped, for example.

The upper portion 110a of the delivery container 110 may include any number of coupling members 114 (e.g., holes) used to secure the delivery container 110 to the rigid container 140 (as will be discussed in further detail below). Additionally, the upper portion 110a of the delivery container 110 may extend a distance upwardly beyond the interior cavity 111. This region may include a gripping portion 115 of a seam that is textured relative to the remainder of the delivery container 110 to assist in safely handling the delivery container 110. In some examples, the gripping portion 115 may also include a handle that allows a user to grab and hold the delivery container 110. Other examples are possible.

The delivery container 110 additionally includes a first drug insertion port 116, at least one secondary drug insertion port 118, and an IV connection port 120 (e.g., delivery port), each of which is in fluid communication with the interior cavity 111 of the delivery container 110. The first drug insertion port 116 and the at least one secondary drug insertion port 118 are used by healthcare professionals to insert the drug 101 into the interior cavity 111 of the delivery container 110 with a needle attached to a syringe or a vial, for example. The IV connection port 120 is adapted to be coupled to a fluid line or tubing (not shown) to administer the drug 101 to a user. In the illustrated example, the ports 116, 118 are positioned at or near the lower portion 110b of the delivery container 110 (and specifically, along the tapered region 112), but in other examples, the ports 116, 118 may be positioned at any location on the delivery container 110.

The first drug insertion port 116 has a first coupling mechanism 116a to accommodate a vial, syringe, or other component used to insert the drug 101 into the cavity 111. In some examples, the first coupling mechanism 116a is in the form of a luer lock mechanism. Similarly, the at least one secondary drug insertion port 118 has a second coupling mechanism 118a to accommodate a vial, syringe, or other component used to insert the drug 101 into the cavity 111. In some examples, the second coupling mechanism 118a is in the form of a closed system transfer device ("CSTD") used to transfer the drug 101 in a sterile environment. In the illustrated example, two secondary drug insertion ports 118 are provided, each of which includes a second coupling mechanism 118a having different dimensions to accommodate different sizes of vials, syringes, or containers. As a result, the delivery container 110 itself may be the CSTD, thereby providing compatibility across different types of vials and coupling mechanisms. In some examples, the second coupling mechanism is in the form of a standard 13 mm port that couples to at least one of a 2 R iso-vial or a 13 mm CSTD. In other examples, the second coupling mechanism may be in the form of a standard 20 mm port that couples to at least one of an iso-vial or a 20 mm CSTD. Other examples are possible.

In some examples, the delivery container 110 is delivered to a healthcare professional in an empty state. In other examples, the delivery container 110 may be pre-filled with a saline solution and/or an intravenous stabilizing solution ("IVSS"). In yet other examples, the delivery container 110 may additionally include a preservative in addition to the saline solution and IVSS. Other examples are possible that may reduce overall preparation time.

Figure 2:
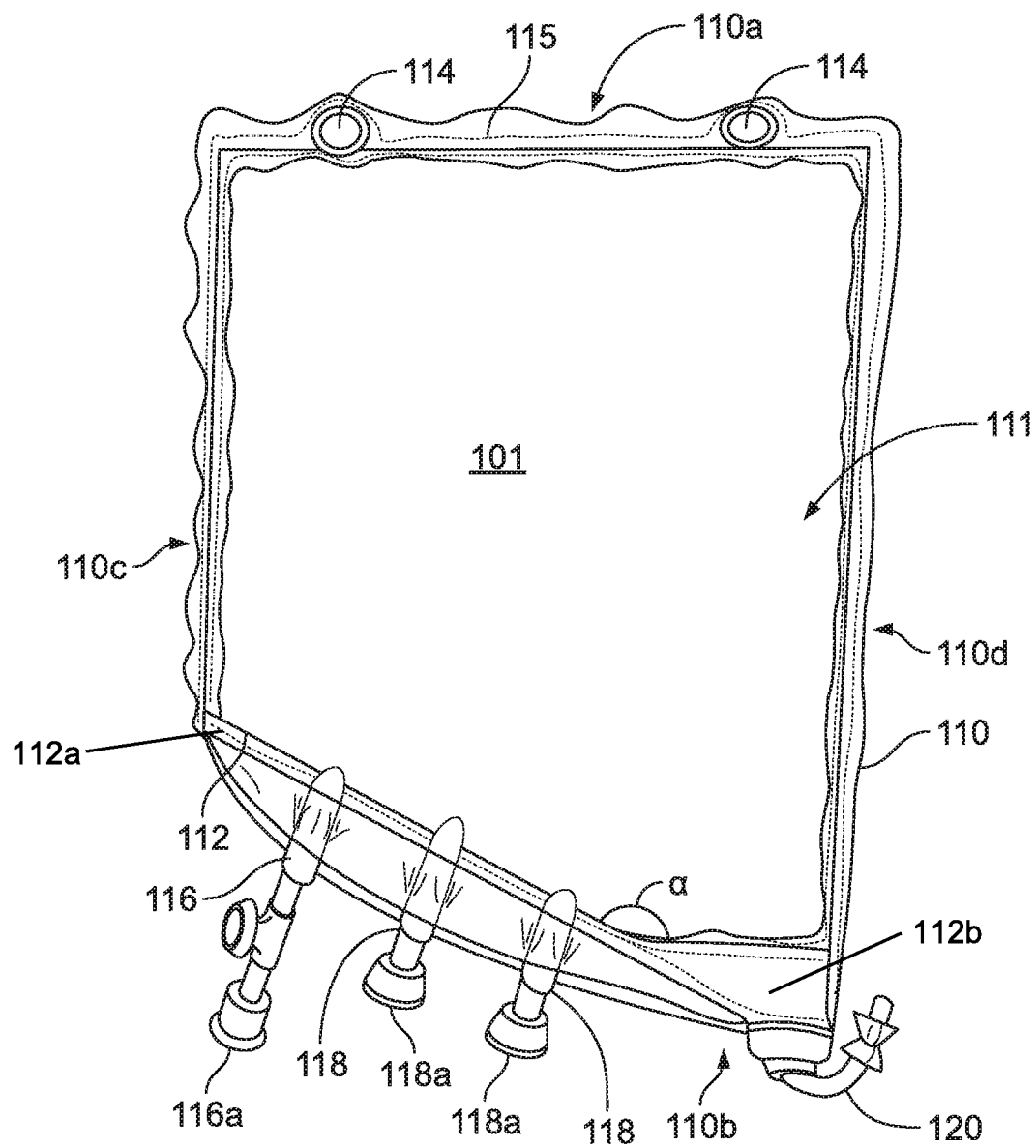
FIG. 2 illustrates an example delivery container for the drug delivery system of FIG. 1 in accordance with various embodiments.

As can be seen in FIG. 2, the IV connection port 120 is positioned at the lower portion 110b of the delivery container 110 and adjacent the lower portion 112b of the tapered region 112 such that, when the drug 101 within the delivery container 110 is being administered to a patient, the entire contents of the delivery container 110 are delivered through the IV connection port 120. As a result, the delivery container 110 reduces and/or eliminates the occurrence of drug hold up, and all of the contents of the delivery container 110 are administered to the user.

Figure 3:
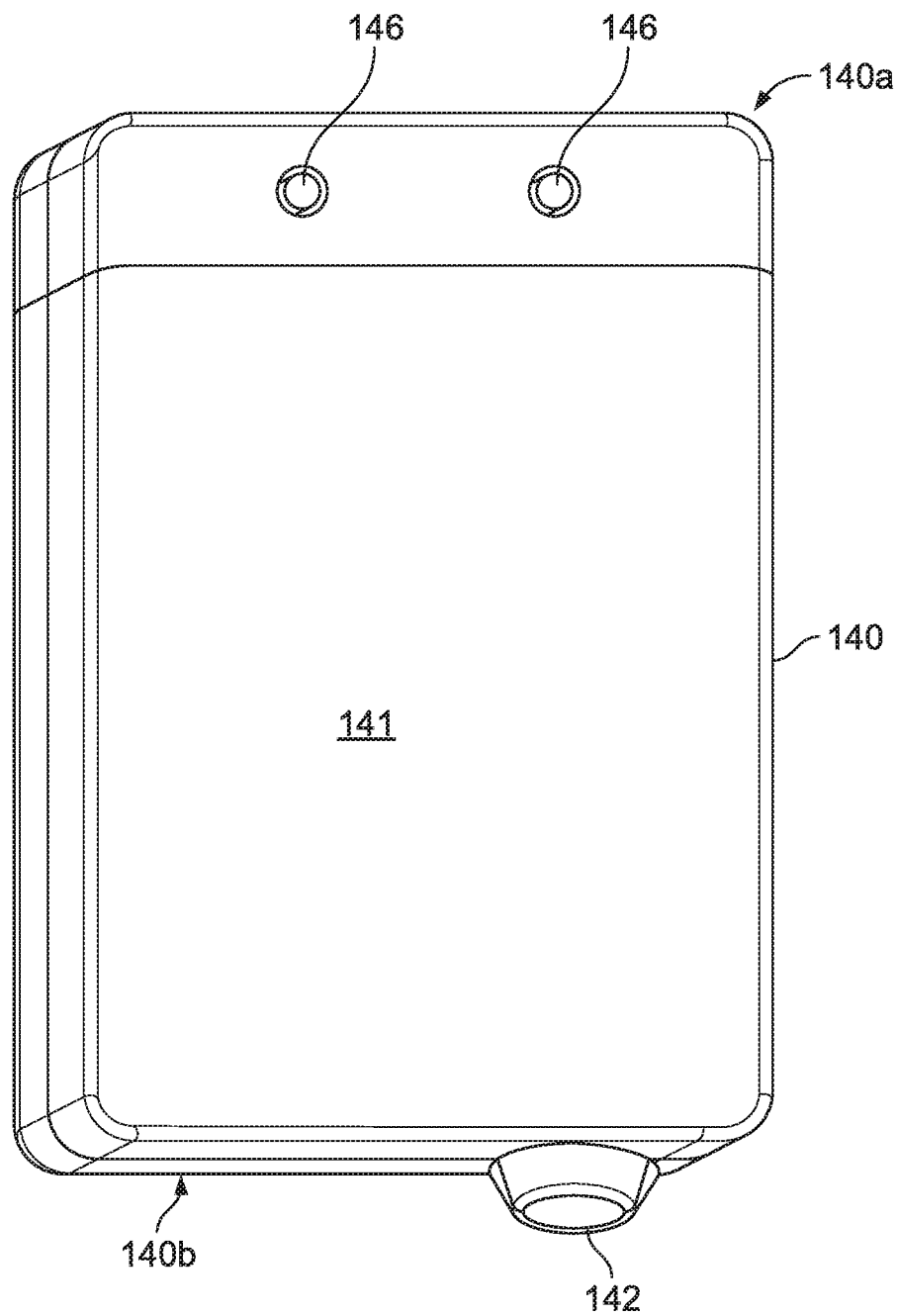
FIG. 3 illustrates an example rigid container for the drug delivery system of FIGS. 1 and 2 in accordance with various embodiments.

Turning now to FIGS. 1 and 3, the rigid container 140 includes an upper portion 140a and a lower portion 140b, and is the form of a shell having an inner volume 141 dimensioned to accommodate the delivery container 110. As illustrated in FIG. 1, the rigid container 140 may be in the form of a hinged or clamshell member that opens to provide access to the inner volume 141. The rigid container 140 is constructed from a rigid material such as a polymer, a metal, etc. that is sufficiently strong to protect the delivery container from damage. The lower portion 140b of the rigid container 140 includes an opening 142 that accommodates a portion of the IV connection port 120 and/or an IV line that exits the IV connection port 120. The rigid container 140 may additionally include padding 144 disposed within the shell to further protect the delivery container 110. As a result the delivery container 110 is protected from the occurrence of punctures from occurring during drug administration.

Positioned at or near the upper portion 140a of the rigid container 140 is at least one mounting portion 146 in the form of a mounting post. The mounting post 146 is dimensioned to be inserted into the coupling member 114 of the delivery container 110, thereby further securing the delivery container 110 within the rigid container 140. The mounting post may extend upwardly from the front and/or the rear portion of the rigid container 140, and may include a notched portion along its length that accommodates the coupling member 114 of the delivery container 110. In some examples, the mounting post may be in the form of two distinct sections with one section being coupled to the front portion of the rigid container 140 and another section being coupled to the rear portion of the rigid container 140 that couple together (e.g., via a frictional connection, a snap fit, etc.) to secure to the coupling member 114 of the delivery container 110. In these examples, the coupling member 114 may simply be a portion of the delivery container 110 that is held in place by the two distinct sections. The two distinct sections may have end regions that mate together (e.g., via a protrusion and corresponding socket) in a way that the coupling member 114 of the delivery container 110 is also urged into the socket.

In some examples, the rigid container 140 may also include a securing strap member 148 which may be constructed from an elastic material. The delivery container 110 may be inserted into the inner volume 141 of the rigid container 140 below the securing strap member 148 such that the securing strap member 148 maintains the delivery container 110 against the rear wall thereof.

In some examples, the rigid container 140 may additionally include an upper opening 150 positioned at the upper portion 140a to allow a portion of the upper portion 110a of the delivery container 110 to pass through. The upper opening 150 may be in the form of a slot that may include securement features such as teeth or prongs to secure the upper portion 110a of the delivery container 110. In some approaches, the upper opening 150 may also include a feeding mechanism such as rollers to advance the delivery container 110 upwards. As a result, a user may grasp the gripping portion 115 of the delivery container instead of grasping the entire rigid container. In some examples, the rigid container 140 may additionally include any number of external securement features. For example, an external strap (not shown) may act as a belt loop that secures the rigid container to a user's waist region. Other examples are possible.

So configured, the described drug delivery system 100 makes it easier to change out delivery containers 110 quickly, along with ensuring that all or most of drug 101 is actually delivered to the patient because the shape and configuration of the container 110 including the tapered region 112 allows the drug to naturally flow to and out of the IV connection port 120. By including a number of different ports having different coupling mechanisms, healthcare professionals can also quickly and easily fill the delivery container 110 with the required drug, and needn't keep a large number of connection mechanisms (e.g., 10-15 conventional CSTD devices) in stock.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies;

Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153, 507); Tysabri® (natalizumab, anti-α4integrin mAb); Valortim® (MDX-1303, anti-B. anthracis protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BiTE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery system comprising:
    a delivery container including an upper portion, a lower portion, a first side portion, a second side portion, and a tapered region extending between the first side portion and the second side portion, the delivery container further including an interior cavity, the tapered region including a surface area between seams defining the interior cavity;
    a first drug insertion port positioned at the lower portion of the delivery container through the surface area of the tapered region, the first drug insertion port having a luer lock;
    at least one additional drug insertion port positioned at the lower portion of the delivery container through the surface area of the tapered region, the at least one additional drug insertion port not having a luer lock; and
    an IV connection port positioned at the lower portion of the delivery container adjacent to a lower portion of the tapered region, wherein the surface area is downwardly angled from the first side portion toward the IV connection port.

2. The drug delivery system of claim 1, wherein the additional drug insertion port comprises at least one of: a standard 13 mm port or a standard 20 mm port.

3. The drug delivery system of claim 1, further comprising a rigid container defining an inner volume, the rigid container having an upper portion and a lower portion, the lower portion of the rigid container including an opening to accommodate at least one of the IV connection port or an IV line.

4. The drug delivery system of claim 3, wherein the delivery container further includes at least one opening formed in the upper portion thereof, the rigid container further including at least one mounting post dimensioned to receive the at least one opening of the delivery container to operably secure the delivery container within the inner volume of the rigid container.

5. The drug delivery system of claim 3, wherein the rigid container further includes at least one securing strap member.

6. The drug delivery system of claim 3, wherein the rigid container includes an opening at the upper portion thereof to accommodate a portion of the delivery container.

7. The drug delivery system of claim 1, wherein the delivery container is empty.

8. The drug delivery system of claim 1, wherein the delivery container contains a saline solution and an intravenous stabilizing solution.

9. The drug delivery system of claim 8, wherein the delivery container further contains a preservative.

10. The drug delivery system of claim 1, wherein the delivery container has a trapezoidal shape.

11. The drug delivery system of claim 1, wherein the tapered region is disposed at an angle between 100 and 150 degrees relative to the lower portion.

12. A drug delivery system comprising:
    a delivery container including an upper portion, a lower portion, a first side portion, a second side portion, and a tapered region extending between the first side portion and the second side portion, the delivery container including at least one opening formed in the upper portion thereof, the delivery container further including an interior cavity, the tapered region including a surface area between seams defining the interior cavity;
    a first drug insertion port positioned at the lower portion of the delivery container, the first drug insertion port having a luer lock;
    at least one additional drug insertion port positioned at the lower portion of the delivery container, the at least one additional drug insertion port not having a luer lock, wherein at least one of the first drug insertion port and the at least one additional drug insertion port is positioned through the surface area of the tapered region;

an IV connection port positioned at the lower portion of the delivery container adjacent to a lower portion of the tapered region; and a rigid container defining an inner volume, the rigid container having an upper portion and a lower portion, the upper portion including at least one mounting post dimensioned to receive the at least one opening of the delivery container to operably secure the delivery container within the inner volume of the rigid container, the lower portion of the rigid container including an opening to accommodate at least one of the IV connection port or an IV line, wherein the surface area is downwardly angled from the first side portion toward the IV connection port.

13. The drug delivery system of claim 12, wherein the additional drug insertion port comprises at least one of:

a standard 13 mm port; or a standard 20 mm port.

14. The drug delivery system of claim 12, wherein the rigid container further includes at least one securing strap member.

15. The drug delivery system of claim 12, wherein the rigid container includes an opening at the upper portion thereof to accommodate a portion of the delivery container.

16. The drug delivery system of claim 12, wherein the delivery container is empty.

17. The drug delivery system of claim 12, wherein the delivery container contains a saline solution and an intravenous stabilizing solution.

18. The drug delivery system of claim 17, wherein the delivery container further contains a preservative.

19. The drug delivery system of claim 12, wherein the delivery container has a trapezoidal shape.

* * * * *